US00PP19657P3

(12) United States Plant Patent
Huisman

(10) Patent No.: US PP19,657 P3
(45) Date of Patent: Jan. 20, 2009

(54) ***CAMPSIS* PLANT NAMED 'TARANTELLA'**

(50) Latin Name: *Campsis radicans*
Varietal Denomination: Tarantella

(76) Inventor: Marinus Huisman, Veldlaan 70, Boskoop, 2771 LZ (NL)

( * ) Notice: Subject to any disclaimer, the term of this patent is extended or adjusted under 35 U.S.C. 154(b) by 0 days.

(21) Appl. No.: 12/012,624

(22) Filed: Feb. 4, 2008

(65) Prior Publication Data

US 2008/0189815 P1 Aug. 7, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
*Assistant Examiner*—S. B. McCormick Ewoldt

(57) ABSTRACT

A new and distinct cultivar of *Campsis* named 'TARANTELLA that is characterized by upright compact habit, glossy green leaves, and many reddish-orange flowers to a flowering stem. In combination these traits set 'TARANTELLA apart from all other existing varieties of *Campsis* known to the inventor.

4 Drawing Sheets

Genus: *Campsis*.
Species: *radicans*.
Denomination: 'TARANTELLA'.

CLAIM OF PRIORITY

This application claims the benefit of priority under 35 U.S.C. 119(f) of the application for a grant of European Community Plant Breeders Rights which was filed for the instant plant variety on Feb. 5, 2007 and which was first published on Apr. 15, 2007, Application Number 2007/0330.

BACKGROUND OF THE INVENTION

The present invention relates to a new and distinct cultivar of trumpet creeper that is grown for use as an ornamental landscape plant. The new cultivar is known botanically as *Campsis radicans* and will be referred to hereinafter by the cultivar name 'TARANTELLA'.

The inventor has been interested in the genus *Campsis* since 1991 and maintains a collection of named cultivars and unnamed selections which have arisen at the inventor's nursery in Boskoop, The Netherlands. The inventor maintains the collection as a resource for deliberate open pollination as explained further below. The inventor's intention is to identify useful new hybrids of *Campsis* which combine the commercial attributes of plant hardiness, a slow rate of growth, and well-presented attractive inflorescences. The inventor has introduced other new varieties of *Campsis* to commerce, including the variety 'HUIDAN' (U.S. Plant Pat. No. 16,656).

In 2000, the inventor removed the male reproductive organs from a group of unnamed plants of *Campsis grandiflora*. The inventor held these emasculated plants in a greenhouse and hand-pollinated them using pollen which the inventor had collected from unnamed selections of *Campsis radicans*. By September 2000, the inventor was able to collect seeds and set them aside for sowing in the following year.

Ordinarily, *Campsis* plants grow very rapidly, especially in greenhouses, and the inventor was readily able to identify 'TARANTELLA' as a distinctively slower-growing variety. The inventor selected 'TARANTELLA' in 2001 for this useful characteristic.

The closest known comparison plant in commerce, known to the breeder, is the variety 'HUIDAN' (U.S. Plant Pat. No. 16,656). Comparisons may also be drawn with the two parent species (unpatented).

'TARANTELLA' differs from the male parent *Campsis radicans* as follows:

Whereas 'TARANTELLA' bears large red-orange flowers, the flowers of *Campsis radicans* are small and red. The racemes of 'TARANTELLA' are also longer than the racemes of *Campsis radicans*.

'TARANTELLA' differs from the female parent *Campsis grandiflora* as follows:

Whereas 'TARANTELLA' bears large red-orange flowers, the flowers of *Campsis grandifora* are light orange. 'TARANTELLA' exhibits improved hardiness when compared with *Campsis grandiflora*.

'TARANTELLA' differs from 'HUIDAN' as follows:

Whereas the flowers of 'TARANTELLA' are red-orange in color, the flowers of 'HUIDAN' are red and also smaller in size.

The first asexual reproduction of 'TARANTELLA' was conducted by the inventor in the summer of 2001 in a propagation greenhouse at the inventor's nursery in Boskoop, The Netherlands. The method used was softwood cuttings. Since that time 'TARANTELLA' has been determined fixed, stable and true to type in subsequent generations of asexual propagation.

SUMMARY OF THE INVENTION

The following represent the distinguishing characteristics of the new *Campsis* cultivar 'TARANTELLA. In combination these traits set 'TARANTELLA apart from all other existing varieties of *Campsis* known to the inventor. 'TARANTELLA has not been tested under all possible conditions and phenotypic differences may be observed with variations in environmental, climatic, and cultural conditions, however, without any variance in genotype.

1. *Campsis* 'TARANTELLA' is a perennial that blooms midsummer to fall.
2. *Campsis* 'TARANTELLA' exhibits an upright habit.
3. *Campsis* 'TARANTELLA' exhibits many flowers per flowering stem.
4. *Campsis* 'TARANTELLA' produces reddish-orange trumpet-shaped flowers.
5. *Campsis* 'TARANTELLA' exhibits glossy dark-green leaves.
6. *Campsis* 'TARANTELLA' is a semi-evergreen vine.
7. *Campsis* 'TARANTELLA' is 35 cm. in diameter and 65 cm in height after one growing season and approximately 5 m in height at maturity.
8. *Campsis* 'TARANTELLA' is hardy to USDA Zone 7.
9. *Campsis* 'TARANTELLA' is an ornamental landscape plant suitable for use on trellis, wall, or as a screen in the landscape.

BRIEF DESCRIPTION OF THE DRAWINGS

The accompanying color drawings illustrate the overall appearance of the new *Campsis* cultivar named 'TARANTELLA' showing color as true as is reasonably possible to obtain in color reproductions of this type. Color in the drawings may differ from color values cited in the detailed botanical description, which accurately describe the actual color of the new variety 'TARANTELLA'. The drawings were made of 1-year-old plant growing in 14 cm containers.

The drawing labeled

The drawing labeled

The drawing labeled

The drawing labeled

Figure 1:
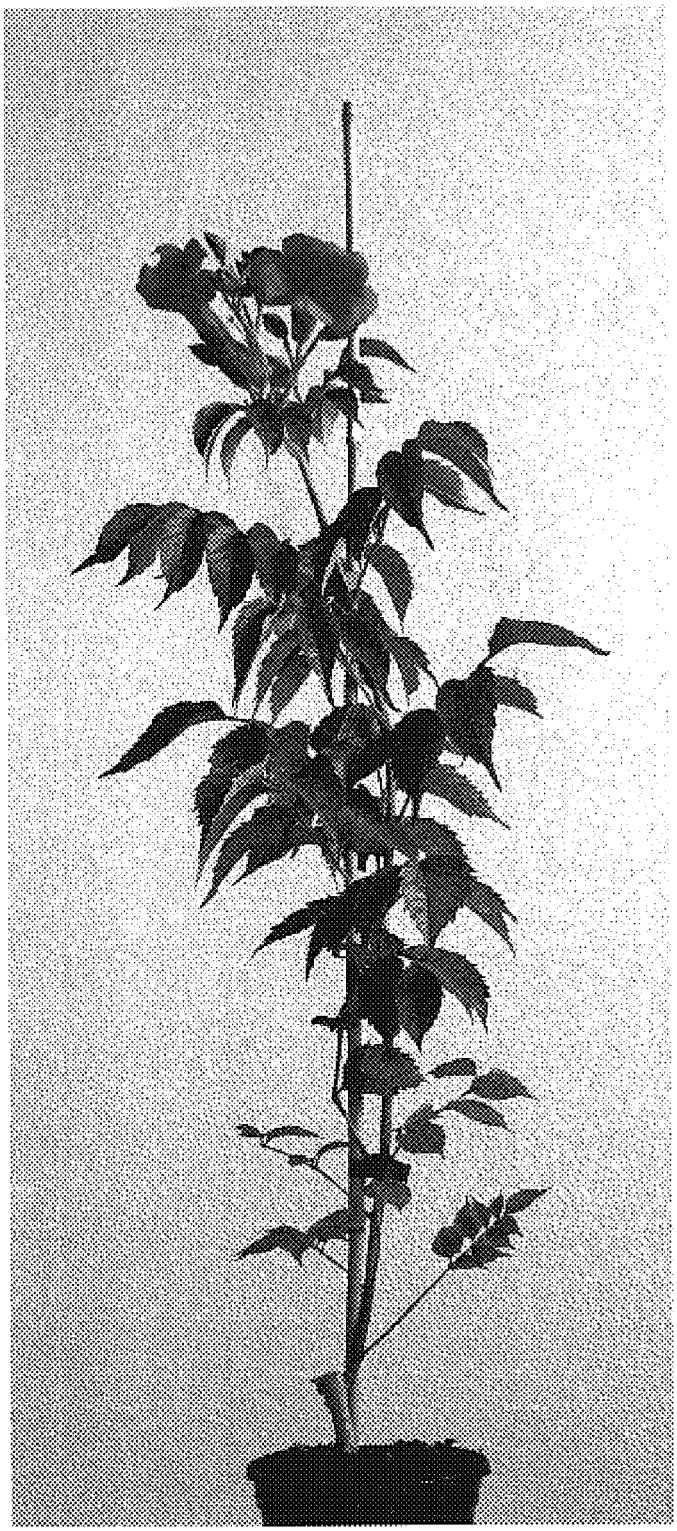
FIG. 1 depicts a single plant of 'TARANTELLA' in bloom illustrating habit and overall appearance.
Figure 2:
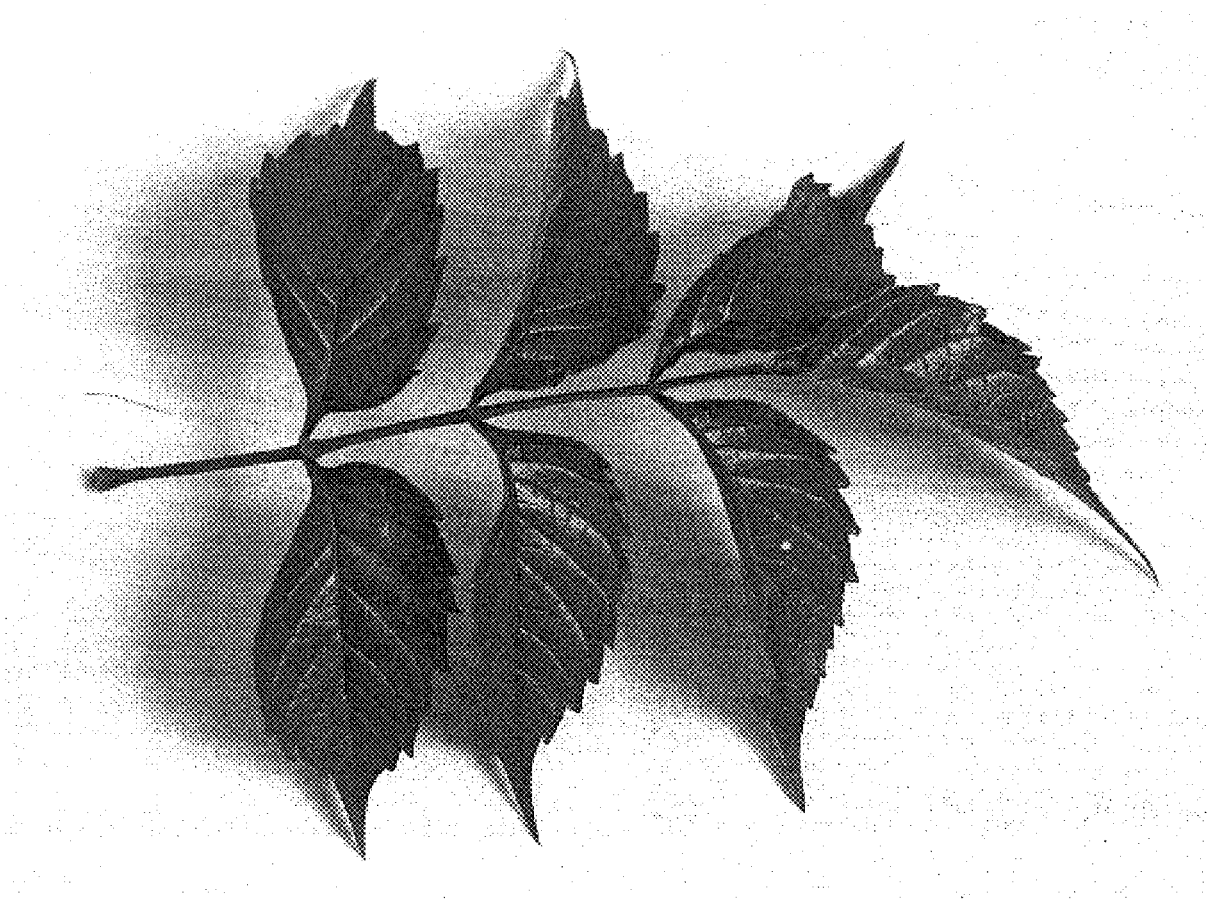
FIG. 2 depicts a close-up view of the foliage of 'TARANTELLA'.
Figure 3:
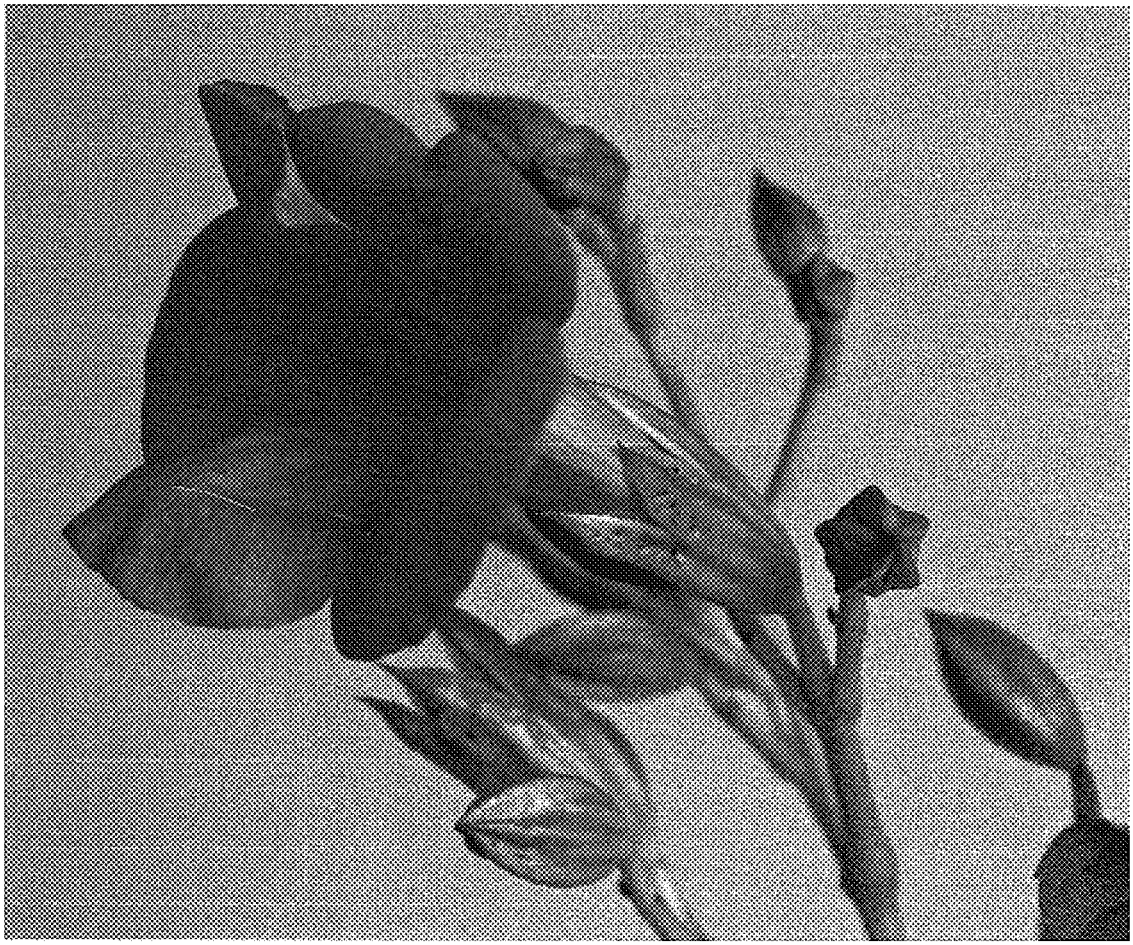
FIG. 3 depicts a close up side view of the inflorescence of 'TARANTELLA' showing one open flower and buds at varying stages of development.
Figure 4:
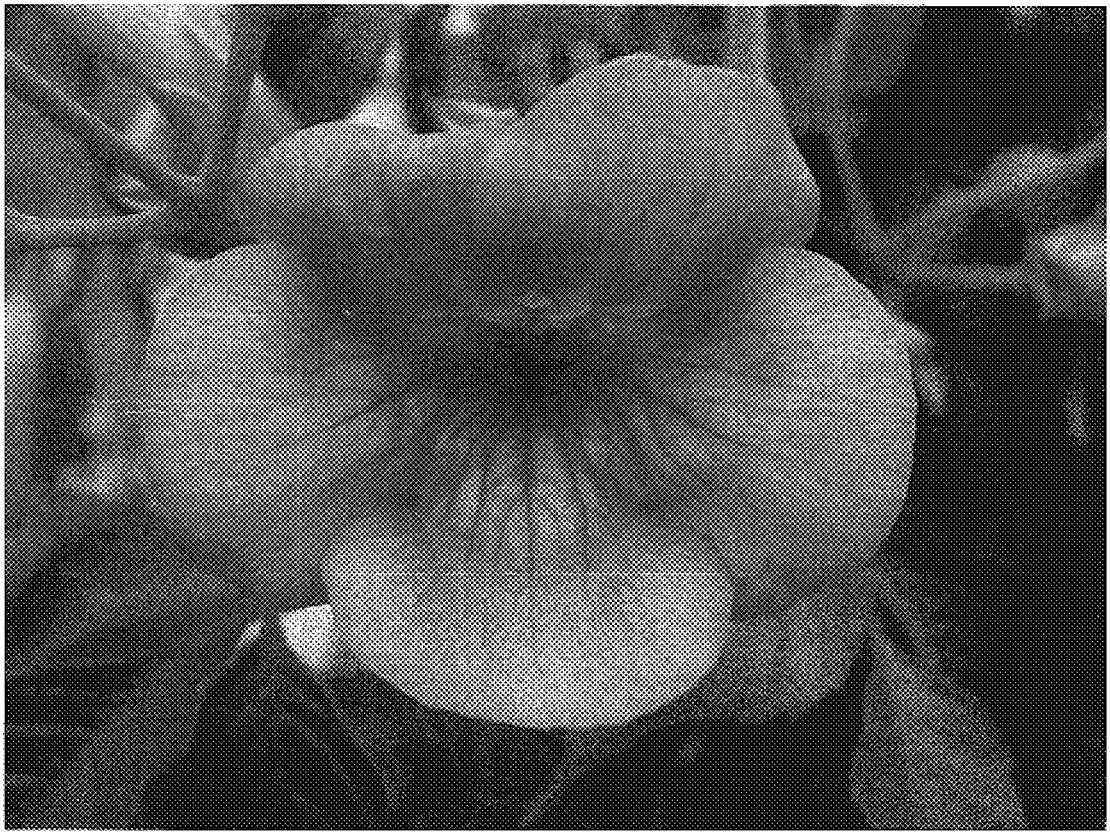
FIG. 4 depicts a front view of a flower of 'TARANTELLA'.

Drawings were made using conventional techniques and although flower and foliage color may appear different from actual color due to light reflectance, they are as accurate as possible by conventional photography.

DETAILED BOTANICAL DESCRIPTION OF THE PLANT

The following is a detailed description of the *Campsis* cultivar named 'TARANTELLA'. Data was collected by the inventor in Boskoop, The Netherlands from 12-month-old plants, in August, that were grown out-of-doors in 1-liter containers. The average daytime temperatures were 14° C. to 28° C. with normal outdoor light level, and the average nighttime temperatures were 7° C. to 16° C. Color determinations are in accordance with the 2001 Royal Horticultural Society Colour Chart except where general color terms of ordinary dictionary significance are used. The growing requirements are similar to the species and there are no disease problems known to the inventor. No growth retardants or photoperiodic treatments were applied to the plants.

Botanical classification: *Campsis radicans* 'TARANTELLA.
Species: *radicans*.
Common name: Trumpet creeper.
Commercial classification: Vine.
Type: Perennial.
Use: Used as an ornamental for container, trellis, wall, or other structures in the landscape.
Parentage: Open pollinated plants of *Campsis radicans* (male parent) and *Campsis grandiflora* (female parent).
Growth habit: Upright climbing habit.
Growth rate: Grows approximately 20 cm per month in spring.
Plant dimensions: An average of 65 cm in height and 35 cm in width.
Vigor: Moderate.
Hardiness: USDA Zone 7.
High temperature tolerance: At least up to 35° Centigrade.
Recommended crop container size: 14 cm pots.
Propagation: Vegetative cuttings.
Root system: Both underground and aerial roots as later described. Fine aerial rootlets.
Cultural requirements: Plant in full sun or partial shade, and well-drained soil with regular to moderate water.
Seasonal interest: Reddish-orange flowers from midsummer to fall.
Time to develop to commercial container size: An average of 6 months is needed to produce a 14-cm container plant from a cutting.
Special growing requirements or growing problems: None known to the inventor.
Disease and pest susceptibility: No susceptibility to disease and pests known to the inventor.

*Stem.*—Branching habit: Compact basal branching and lateral branching. Dimensions: 57 cm in length and 6 mm in diameter. Strength: Strong. Shape: Cylindrical. Surfaces: Glabrous. Pubescence: None observed. Internode length: 6.9 cm. Color, younger stems: 143B. Color, older bark: N199A and N199B. Lenticels: Present. Lenticel shape: Lens-shaped. Lenticels quantity: Average of 15 per cubic centimeter. Lenticel dimensions: An average of 0.75 mm in length and 0.4 mm. in width. Lenticel color: 161A.

Foliage:

*Type.*—Semi-evergreen.
*Leaf arrangement.*—Opposite.
*Leaf division.*—Compound.
*Leaf shape.*—Pinnate.
*Leaves per lateral branch.*—Average number of 18 leaves or 9 pairs.
*Quantity of leaflets per leaf.*—A range of 5–9 leaflets per leaf.
*Leaflet.*—Margin: Entire. Shape: Ovate. Apex: Apiculate. Base: Attenuate. Dimensions: An average of 8.0 cm in length and 3.7 cm in width. Surface (adaxial and abaxial surfaces): Smooth, young leaves slightly glossy; mature leaves glossy. Appearance: Glossy. Margin: Serrate. Young leaflet color (adaxial surface): 141A. Young leaflet color (abaxial surface): 144A. Mature leaflet color (adaxial surface): Between 137A and 147A, closer to 137A. Mature leaflet color (abaxial surface): 144A. Venation pattern: Pinnate. Vein color (adaxial surface): 144A. Vein color (abaxial surface): 144B. Pubescence: Mostly glabrous with only a few short hairs on veins on abaxial surface. Petioles: Absent (only a rachis). Leaf attachment: Rachis. Rachis dimensions: An average of 13.1 cm in length and 2 mm in diameter. Rachis color: 143A. Durability: High durability to stress. Stipules, tendrils, thorns: Absent.

Inflorescence:

*Flower arrangement.*—Terminal thyrse.

*Type of inflorescence.*—Thyrse.

*Inflorescence dimensions.*—An average of 13.2 cm in height and 16.8 cm in width.

*Quantity of flowers per inflorescence.*—An average of 33 flowers per inflorescence.

*Blooming period.*—Blooms continuously from late July to September.

*Quantity of buds per flowering stem.*—An average of 30 buds per flowering stem.

*Quantity of buds and flowers per plant.*—An average of 33 buds and flowers per plant.

*Natural flowering season.*—Summer.

*Response time.*—Approximately 9 months for field grown plant to flower.

*Rate of flower opening.*—Approximately 10% of the flowers are open at any stage.

*Fragrance.*—None observed.

*Bud.*—Dimensions: 3 cm in length and 1.2 cm in diameter Flower bud shape: Elliptic with an apiculate top; upper half has 5 longitudinal ribs (seen from above: "star-like"). Flower bud color: 152B with base 153A and 153B.

*Flower aspect.*—Facing outward and upward.

*Shape of flower.*—Trumpet-shaped.

*Dimensions of flower.*—An average of 7.2 cm in diameter and 7.8 cm in depth.

*Lastingness of flower on plant.*—Approximately 5 days.

*Persistent or self-cleaning.*—Self-cleaning.

*Petal.*—Surface (adaxial and abaxial surface): Dull, smooth. Appearance (adaxial and abaxial surface): Trumpet-shaped. Number: 5. Fused or unfused: Lower ¾ of the petals basally fused; upper ¼ is free Shape: Flabellate. Margin: Entire (the larger part is fused). Apex: Very shallow retuse to very shallow praemorse. Dimensions: An average of 7.8 cm in length and 3.8 cm in width. Color when opening (adaxial surface): 42C; tube 43B and 43C, veins 46A and 46B Color when opening (abaxial surface): 35A; tube 31B Color, fully opened (adaxial surface): 42C and 42D; tube 32B and 32D. Color, fully opened (abaxial surface): 35B; tube 24A and 24B. Fading petal color: No fading observed. Petaloids: None.

*Sepals.*—Appearance: Dull, smooth Arrangements: Fused into a campanulate calyx, upper ⅖ is free, lower ⅗ is fused. Number: Five. Shape: Narrow elliptic. Margin: Entire. Tip: Short acuminate. Base: Fused. Dimensions: An average of 3.5 cm in length and 7 mm in width. Color, immature (adaxial): 153D. Color, immature (abaxial): 152B; base 153A and 153B. Color, mature (adaxial): 153A and 153B. Color, mature (abaxial): 11A and 11B.

*Calyx.*—(Shape: Campanulate. Dimensions: 3.5 cm in length and 1.8 cm in width.

*Peduncle.*—Dimensions: An average of 12.8 cm in length and 3 mm in diameter Peduncle angle: Straight upright, 0° angle. Peduncle strength: Strong. Peduncle color: 144A.

*Pedicel.*—Dimensions: An average of 1.1 cm in length and 3 mm in diameter. Angle: Straight upright, 0° to 30°. Strength: Strong Color: N144A

*Reproductive organs.*—Stamens: 4 in number. Stamen shape: Dorsifixed, narrow elliptic, v-shaped. Anther length: 4 mm. Average filament length: 2.8 mm. Anther color: 11B. Amount of pollen: Average. Pistil number: 1 Pistil length: An average of 4.3 cm. Stigma shape: Flattened ovate. Stigma color: Ovate. Style length: An average of 4 cm. Style color: 144C and 144D. Ovary color: 144C.

*Seed.*—No seed production has been observed to date.

It is claimed:

1. A new and distinct variety of *Campsis* plant named 'TARANTELLA as described and illustrated herein.

* * * * *